(12) United States Patent
Nodtvedt

(10) Patent No.: US 9,046,701 B2
(45) Date of Patent: Jun. 2, 2015

(54) SPECTACLE ATTACHMENT THAT PROVIDES PROTECTION

(71) Applicant: Century Pacific Medical, Inc., Aliso Viejo, CA (US)

(72) Inventor: Victor Nodtvedt, Irvine, CA (US)

(73) Assignee: Century Pacific Medical, Inc., Aliso Viejo, CA (US)

( * ) Notice: Subject to any disclaimer, the term of this patent is extended or adjusted under 35 U.S.C. 154(b) by 124 days.

(21) Appl. No.: 13/793,134

(22) Filed: Mar. 11, 2013

(65) Prior Publication Data

US 2014/0253862 A1    Sep. 11, 2014

(51) Int. Cl.
| G02C 7/10 | (2006.01) |
| G02C 11/00 | (2006.01) |
| A42B 1/06 | (2006.01) |
| A61F 9/02 | (2006.01) |

(52) U.S. Cl.
CPC ............... *G02C 11/12* (2013.01); *A42B 1/066* (2013.01); *A61F 9/029* (2013.01)

(58) Field of Classification Search
CPC ............ G02C 7/10; G02C 7/16; G02C 7/165; G02C 9/04; G02C 11/12; A61F 9/029; A42B 1/066; A42B 1/067
USPC .............. 351/41, 44, 158, 46; 2/13, 448, 449, 2/172
See application file for complete search history.

(56) References Cited

U.S. PATENT DOCUMENTS

| | | | |
|---|---|---|---|
| 3,932,031 A | 1/1976 | Johnston | |
| 4,105,304 A * | 8/1978 | Baker | ................................. 351/47 |
| 4,218,777 A * | 8/1980 | Munnikhuysen | ....................... 2/9 |
| 4,298,991 A | 11/1981 | Recenello | |
| 4,726,075 A | 2/1988 | Hinrichs | |
| 4,751,746 A | 6/1988 | Rustin | |
| 5,206,956 A | 5/1993 | Olson | |
| 5,274,847 A | 1/1994 | Lauttamus | |
| 5,394,567 A | 3/1995 | Vatterott | |
| 5,666,664 A * | 9/1997 | Hamilton | ............................. 2/13 |
| 5,704,063 A | 1/1998 | Tilden | |
| 5,798,815 A | 8/1998 | Hirschman et al. | |
| 5,940,161 A | 8/1999 | Hirschman et al. | |
| RE37,530 E | 1/2002 | Hirschman et al. | |
| 6,393,609 B1 | 5/2002 | Simmons, Sr. | |

(Continued)

FOREIGN PATENT DOCUMENTS

WO     2014164852 A1    10/2014

OTHER PUBLICATIONS

International Search Report and Written Opinion for International Application PCT/US14/23628, completed Jul. 10, 2014, 8 pgs.

*Primary Examiner* — Huy K Mai
(74) *Attorney, Agent, or Firm* — KPPB LLP

(57) ABSTRACT

Systems and methods in accordance with embodiments of the invention implement spectacle attachments that can provide protection from radiation. In one embodiment, a spectacle attachment that provides protection from radiation includes: a body of material that is a barrier to at least some form of radiation; where the body of material is configured so that it can couple with either temple of a pair of glasses; and where the body of material is sized to protect the side of a wearer's face from at least approximately the wearer's temple to approximately below the wearer's cheek when the body of material is coupled to a temple of a pair of glasses and the pair of glasses is worn.

9 Claims, 8 Drawing Sheets

(56) References Cited

U.S. PATENT DOCUMENTS

| | | |
|---|---|---|
| 6,540,347 B1 | 4/2003 | Radziwon et al. |
| 7,527,372 B1 | 5/2009 | Jung |
| 7,862,165 B2 | 1/2011 | Hobbs |
| 8,087,774 B2 | 1/2012 | Yang |
| 2011/0239347 A1 | 10/2011 | Beliveau |
| 2013/0180021 A1* | 7/2013 | Danner .................. 2/172 |

* cited by examiner

SPECTACLE ATTACHMENT THAT PROVIDES PROTECTION

FIELD OF THE INVENTION

The present invention generally relates to spectacle attachments that provide a barrier to at least some form of radiation (such as for example visible light, infrared radiation, or UV radiation), and can thereby protect their users from the sun.

BACKGROUND

Many people enjoy outdoor activities. For example, many people enjoy attending outdoor sporting events such as professional or collegiate football games. Unfortunately, exposure to the sun may accompany such activities, and may result in inconvenience, discomfort, and even a deleterious effect on exposed skin. For example, visible light from the sun may cause glare, UV radiation from the sun may facilitate the development of skin cancer, and radiation generally from the sun may result in heating that can cause discomfort. People typically protect themselves from such exposure by for example wearing sunglasses, applying sunblock, and/or wearing a baseball cap. However, such solutions may be either inconvenient or insufficient. Therefore, the current state of the art can benefit from a more convenient and a more effective way of providing protection from the sun.

SUMMARY OF THE INVENTION

Systems and methods in accordance with embodiments of the invention implement spectacle attachments that can provide protection from radiation. In one embodiment, a spectacle attachment that provides protection from radiation includes: a body of material that is a barrier to at least some form of radiation; where the body of material is configured so that it can couple with either temple of a pair of glasses; and where the body of material is sized to protect the side of a wearer's face from at least approximately the wearer's temple to approximately below the wearer's cheek when the body of material is coupled to a temple of a pair of glasses and the pair of glasses is worn.

In another embodiment, the body of material is sized to protect a portion of the wearer's head from at least approximately the wearer's temple to approximately some portion of the wearer's neck.

In still another embodiment, the body of material is configured to couple with either temple of a pair of glasses via one of: loops, elastic holes, latches, clips and combinations thereof.

In yet another embodiment, the body of material includes a sleeve so that it can couple with a temple of a pair of glasses.

In yet still another embodiment, material that constitutes the body of material provides protection from one of: ultraviolet radiation, infrared radiation, visible light, and combinations thereof.

In a further embodiment, the material that constitutes the body of material is a fabric.

In a yet further embodiment, the material that constitutes the body of material is polypropylene fabric.

In another embodiment, the body of material is rectangular in shape.

In a further embodiment, the body of material is between approximately 12 inches and 24 inches in length, and between approximately 6 inches and 8 inches in height.

In still another embodiment, the body of material is further configured to interconnect with another spectacle attachment.

In yet another embodiment, the body of material is further configured to interconnect with another spectacle attachment using a magnet that is affixed to the body of material.

In still yet another embodiment, the magnet is sewn within the body of material.

In a still further embodiment, the magnet is sewn onto the exterior of the body of material.

In yet still a further embodiment, the body of material is further configured to interconnect with another spectacle attachment using Velcro.

In another embodiment, the body of material further includes a second sleeve, where the first sleeve is proximate one end along the length of the rectangular body of material, and where the second sleeve is proximate the second opposite end along the length of the rectangular body of material, such that the body of material can couple to either temple of a pair of glasses and thereby provide protection.

In still another embodiment, the body of material is further configured to interconnect with another spectacle attachment.

In yet another embodiment, the body of material is configured to interconnect with another spectacle attachment using at least two magnets that are affixed to the body of material, where a first magnet is disposed proximate one end along the length of the rectangular body of material, where the second magnet is disposed proximate a second opposite end along the length of the rectangular body of material, such that two spectacle attachments that are each coupled to a temple of a pair of glasses that is worn can interconnect either in front of the wearer's face or behind the wearer's head.

In a still further embodiment, the magnets are sewn within the body of material.

In another embodiment, the magnets are sewn onto the body of material.

In yet another embodiment, the body of material further includes a second sleeve, and is sized such that it can couple with each temple of a pair of glasses using each of the two sleeves.

DETAILED DESCRIPTION

Turning now to the drawings, spectacle attachments that include a body of material that is a barrier to at least some form of radiation (such as for example visible light, ultraviolet [UV] radiation, or infrared [IR] radiation), that is sized to protect at least some portion of a user's head, and that is configured to couple with a pair of glasses and thereby protect its user from radiation in accordance with embodiments of the invention are illustrated. In many embodiments, the spectacle attachment includes a body of material that is a barrier to at least some form of radiation that is sized to protect at least the side of a user's face from radiation when worn, and is configured to couple to a temple of a pair of glasses. The body of material can be any suitable shape and can be any suitable material. In a number of embodiments, the body of material is a fabric, and is sized such that its length substantially spans at least the length of a temple of pair of spectacles, and its height is such that it protects the side of a user's face from approximately the temple to approximately below the wearer's cheek when worn. The manner in which the fabric is configured to couple with a temple of a pair glasses can be any suitable manner in accordance with embodiments of the invention. For example: loops may be sewn into the fabric, a sleeve may be sewn into the fabric, elastic holes may be sewn into the fabric, latches may be embedded within the fabric, clips may be embedded within the fabric, etc.

Additionally, in many embodiments, the spectacle attachment is further configured to couple to a second spectacle attachment, such that when two spectacle attachments are worn—one attached to each temple of a pair of glasses—the spectacle attachments may further couple with one another, thereby supporting one another and providing protection for both sides of the face. For example, in a number of embodiments, the spectacle attachments each include a magnetic member, such that when two such spectacle attachments are worn (one on each temple of a pair of glasses), the spectacle attachments may couple to one another via their respective magnetic members (e.g., behind the back of the wearer's neck); in this way, the spectacle attachments can provide protection for both sides of a wearer's face along with the wearer's neck and provide support for one another.

In a number of embodiments, the spectacle attachment includes a fabric that is sized and configured to couple to both temples of a pair of glasses, and thereby protect both sides of a face, and may further protect the neck.

Spectacle attachments for protecting the face in accordance with embodiments of the invention are discussed in greater detail below.

Spectacle Attachments that Couple to a Temple of a Pair of Glasses

Figure 1:
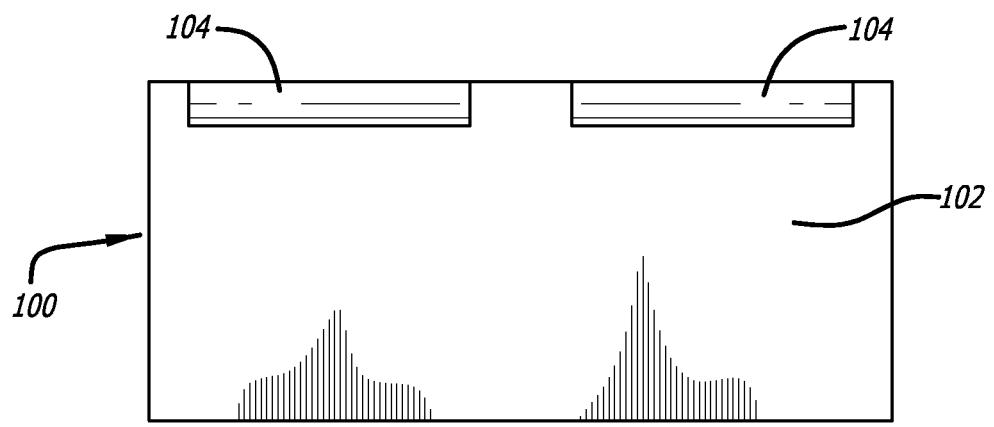
FIG. 1 illustrates a spectacle attachment in accordance with an embodiment of the invention.

Spectacle attachments in accordance with many embodiments of the invention are configured to couple with a temple of a pair of glasses, and include a body of material that is a barrier to at least some form of radiation and is sized to protect at least the side of the user's face from radiation when the pair of glasses is worn. A spectacle attachment that is configured to couple with a temple of a pair of glasses via a sleeve, and includes a pliable material sized to protect at least the side of a wearer's face from radiation when the pair of glasses is worn in accordance with an embodiment of the invention is illustrated in FIG. 1. The spectacle attachment 100 includes a pliable material 102, and sleeves 104 sized to receive a temple of a pair of glasses and thereby removably attach the spectacle attachment to the pair of glasses. The spectacle attachment 100 includes two sleeves 104 so that it can removably attach to either temple of a pair of glasses.

Any material that is a barrier to at least some form of radiation (e.g. visible light, UV radiation, or IR radiation) may be used in accordance with embodiments of the invention; for example, any fabric that can block visible light may be used. In many embodiments, polypropylene fabric is used; polypropylene fabric is advantageous in that it can wick away perspiration and thereby enhance cooling. The fabric may be sized such that it is long enough and tall enough to provide sufficient protection, such as shade, for the side of the face when worn. For example, in some embodiments, the fabric is in the shape of a rectangle where the length of the fabric substantially spans at least the length of a temple of a pair of glasses, and the height of the fabric is such that it drops from the temple to at or below the wearer's cheek when worn. In number of embodiments, the height of the fabric is such that it spans from the temple to the wearer's neck, enabling it to shade, and thereby protect, the side of the face as well as the neck. In many embodiments, the fabric is between 12 and 24 inches long, and between 6 and 8 inches tall. Although a particular shape and dimensions are referenced, any shape with any dimensions that can provide shade to its wearer can be used in accordance with embodiments of the invention. Additionally, although a fabric is referenced, any suitable material can be used.

Moreover, although the illustrated embodiment shows sleeves 104 for coupling the spectacle attachment to a pair of glasses, the spectacle attachment may be coupled to the pair of glasses in any number of ways including using loops, elastic holes, or latches in conjunction with the material sized to provide protection. Additionally, the sleeves may be implemented in any suitable way. For instance, slits may be incorporated in to the hem of a body of material such that sleeves are achieved. Sleeves may also be achieved by incorporating separate sleeve bodies onto the body of material. Additionally, the attachments may be configured to accommodate a variety of temples. For example, the attachments can be elastic so that it can accommodate various temple configurations (e.g. thicker temples). Furthermore, the attachments may allow for convenient and rapid coupling and detachment to a pair of glasses. For example, using sleeves to couple the spectacle attachment to the pair of glasses may allow for convenient and rapid coupling and detachment. Also, in many embodiments, the attachments are configured such that the spectacle attachment can be attached to either temple of a pair of glasses. In the illustrated embodiment, two sleeves 104 are included so that the spectacle attachment 100 can attach to either temple of a pair of glasses. However, this can be achieved in other ways as well. For example, in many embodiments, the spectacle attachment includes sleeves on either side of the fabric, so that the spectacle attachment can be attached to either of the temples. In numerous embodiments, loops are used to couple a spectacle attachment to a pair of glasses, and the loops are disposed such that the spectacle attachment can be attached to either temple of a pair of glasses.

The aforementioned structure of the spectacle attachment can allow it to comfortably and conveniently provide its wearer with protection. For example, in one instance, an intending user may be attending an outdoor professional/collegiate football game during the afternoon. If the intending user is facing north while watching the game, a setting sun may be irradiating the left side of the intending user's face. In this case, the intending user may attach the spectacle attachment to the left temple of a pair of glasses (e.g. sun glasses, prescription glasses, or prescription sun glasses). The spectacle attachment may easily, quickly, and conveniently be coupled with the intending user's pair of glasses. Once coupled, the fabric of the spectacle attachment can shade, and thereby protect, the left side of the user's face, where shade may be especially desired due to the setting sun, and may even protect parts of the user's neck. The spectacle attachment can also block any glare that may be caused by the Sun. If the fabric is a polypropylene fabric (or similar such material), it can wick away any perspiration and thereby further provide cooling. Hence, the spectacle attachment can comfortably and conveniently shade and protect a user's face.

Figure 2A:
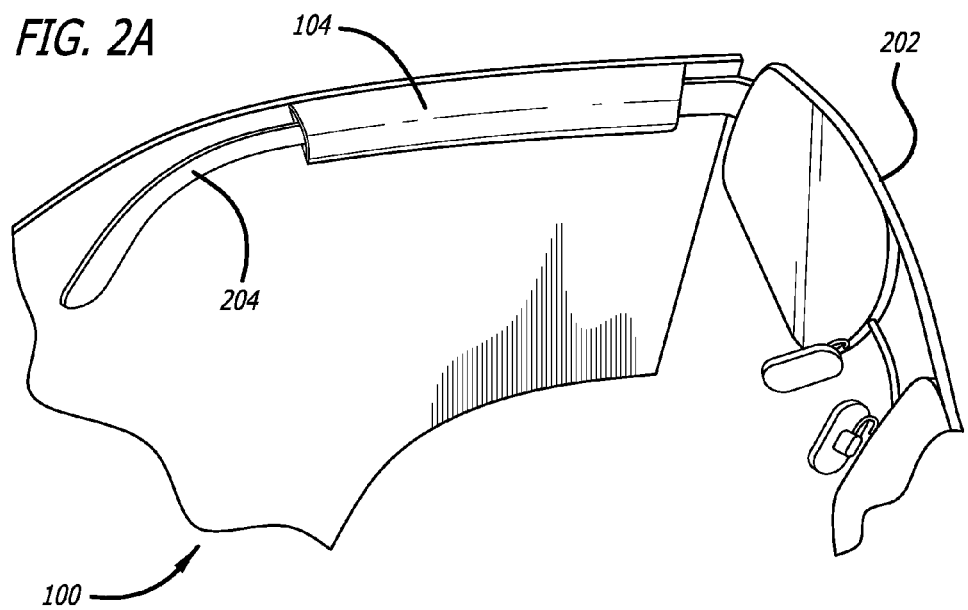
FIGS. 2A and 2B illustrate the wearing of a spectacle attachment in accordance with an embodiment of the invention.
Figure 2B:
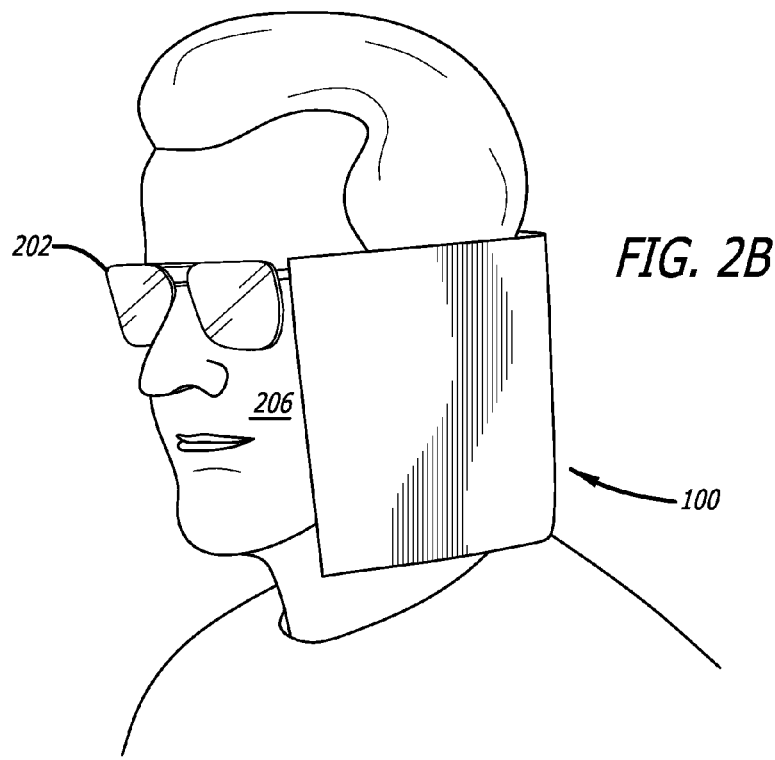

The wearing of a spectacle attachment is illustrated in FIGS. 2A and 2B. The sleeve 104 of a spectacle attachment 100 is coupled with a pair of glasses 202 via a temple 204. The left side of the wearer's face 206 may then be shaded by the spectacle attachment 100 when the pair of glasses 202 are worn. Although the illustrated embodiment depicts the spectacle attachment being worn to shade the left side of the wearer's face, spectacle attachments can of course be implemented and worn so as to shade the right side of a wearer's face in accordance with embodiments of the invention.

Notably, the spectacle attachment does not have to impede the user's direct line of sight, and it may be implemented only when and where it is needed—e.g., if an intending user is facing north against a setting sun, shade may only be needed to protect the left side of a user's face. Thus, the spectacle attachment can provide shade without unnecessary discomfort. Additionally, the material can include graphics and/or text (e.g. advertising or promotional material), and because of the sizing of the material, the graphics and/or text may be sized such that it is visible from afar. For example, the printing on the fabric may demonstrate support for a professional or collegiate football team. Moreover, the spectacle attachment is further advantageous as it can be rapidly detached and reattached as necessary—e.g. if the user briefly visits a concession stand or the restroom. Furthermore, pliable material of the spectacle attachment may allow it to be easily stored when not in use, thereby making it further convenient.

Although particular spectacle attachments that provide shade and couple to a temple of a pair of glasses are described, any of a variety of spectacle attachments that provide shade to the side of a user's face may be implemented in accordance with embodiments of the invention. For example, spectacle attachments that include a material that has dimensions other than between 12 and 24 inches in length and 6 and 8 inches in height may be implemented. In a number of embodiments, a spectacle attachment is further configured to couple with a second spectacle attachment, and these embodiments are discussed below.

Spectacle Attachments that Interconnect

Figure 3:
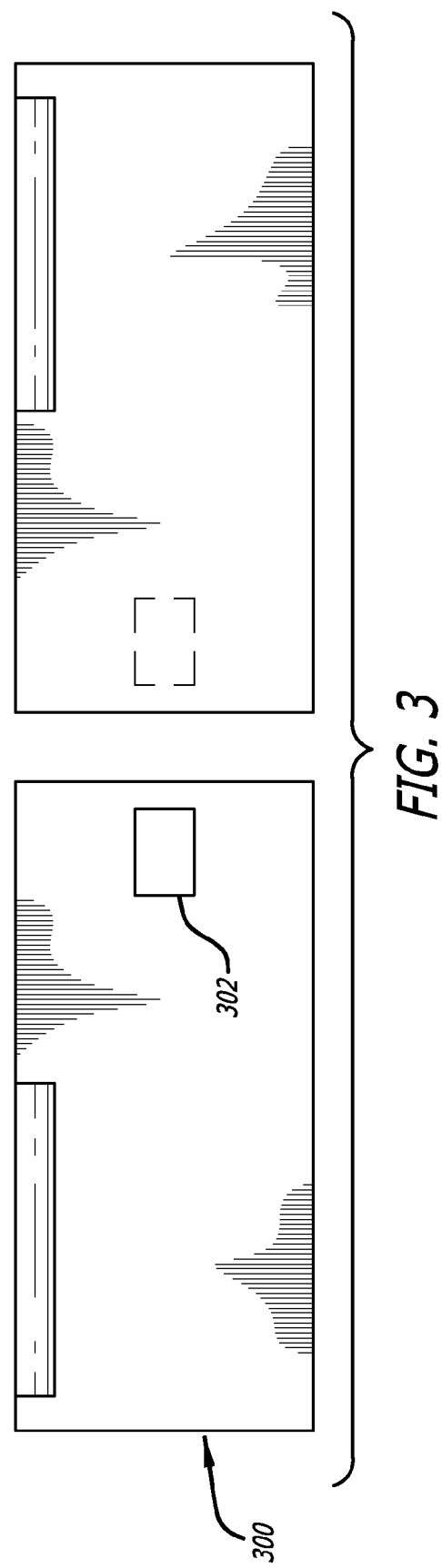
FIG. 3 illustrates a spectacle attachment that is configured to couple with another spectacle attachment in accordance with an embodiment of the invention.
Figure 4:
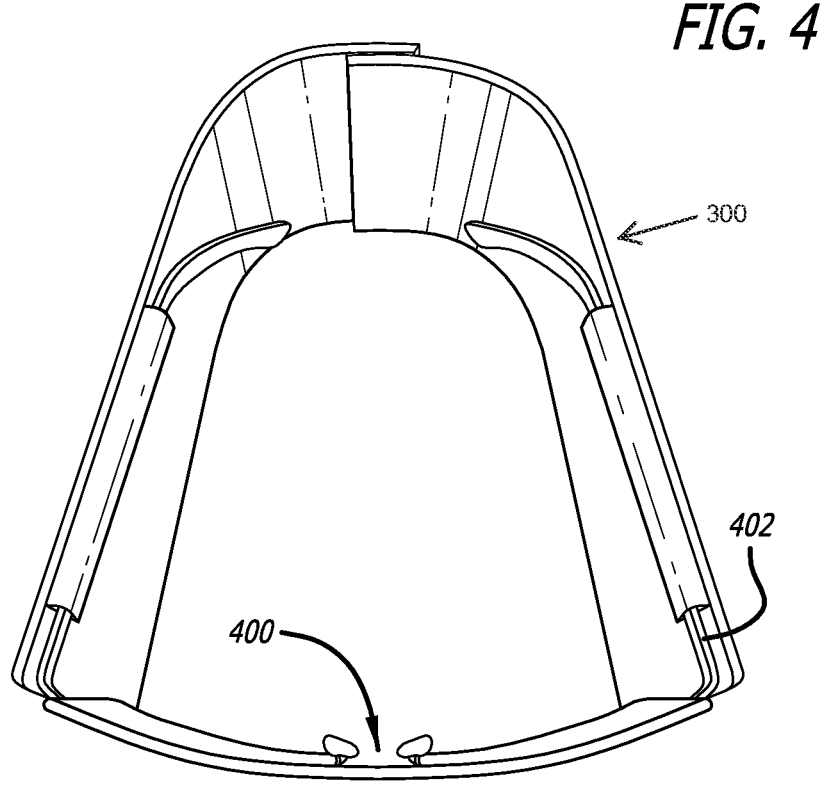
FIG. 4 illustrates the coupling of two spectacle attachments that are configured to couple with one another in accordance with an embodiment of the invention.

Spectacle attachments can be configured to interconnect with other spectacle attachments in accordance with embodiments of the invention. In many embodiments, two spectacle attachments are configured to interconnect with each other when they are each coupled to each of two temples of a pair of glasses. Two spectacle attachments that are configured to interconnect with one another when they are coupled to the temples of a pair of glasses are illustrated in FIG. 3. The spectacle attachments 300 are similar to those described above with respect to FIG. 1 except that they are further configured to attach to one another. In the illustrated embodiment, the spectacle attachments each include a magnetic strip 302, and are configured so that the respective magnetic strips cooperatively interconnect with one another. The magnetic strips can be included in the spectacle attachments in any suitable way; for example, the magnetic strips can be sewn into a body of material that is fabric. In a number of embodiments, the magnetic strips can be sewn onto the exterior of the body of material. Of course, the magnetic strip can be of any suitable dimensions. In many embodiments the magnetic strip is rectangular in shape, between 4 and 6 inches in height and 8 and 12 inches in length. Although in the illustrated embodiment, the spectacle attachments couple to one another via magnetic strips, any suitable means of coupling may be used. For example, in many embodiments, the spectacle attachments can couple with one another via Velcro. The coupling of the spectacle attachments is illustrated in FIG. 4. In particular, the spectacle attachments 300 are coupled to the temples 402 of a pair of glasses 400, and then coupled to one another 300, e.g. via magnets.

Figure 5A:
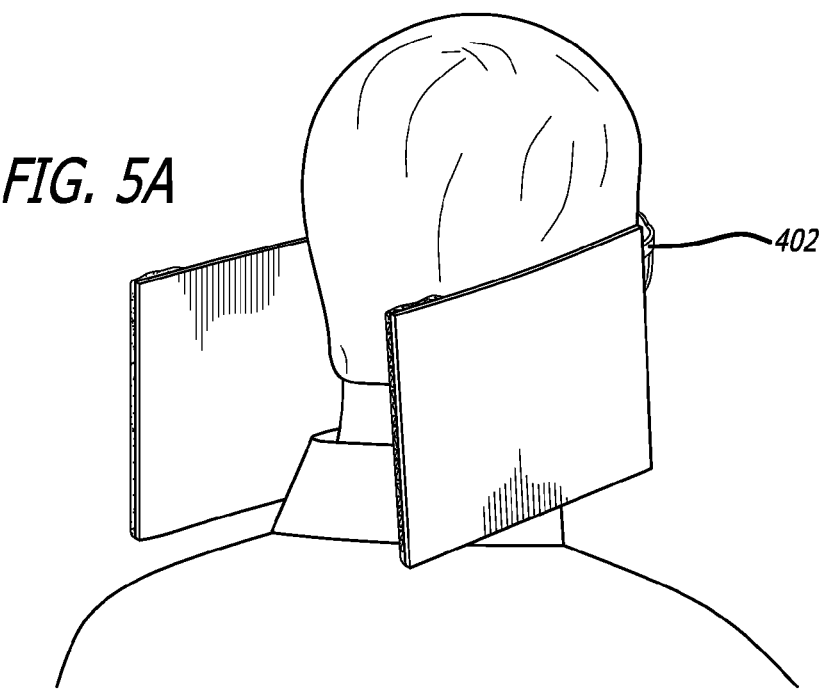
FIGS. 5A and 5B illustrate the wearing of spectacle attachments that are configured to couple with one another in accordance with an embodiment of the invention.
Figure 5B:
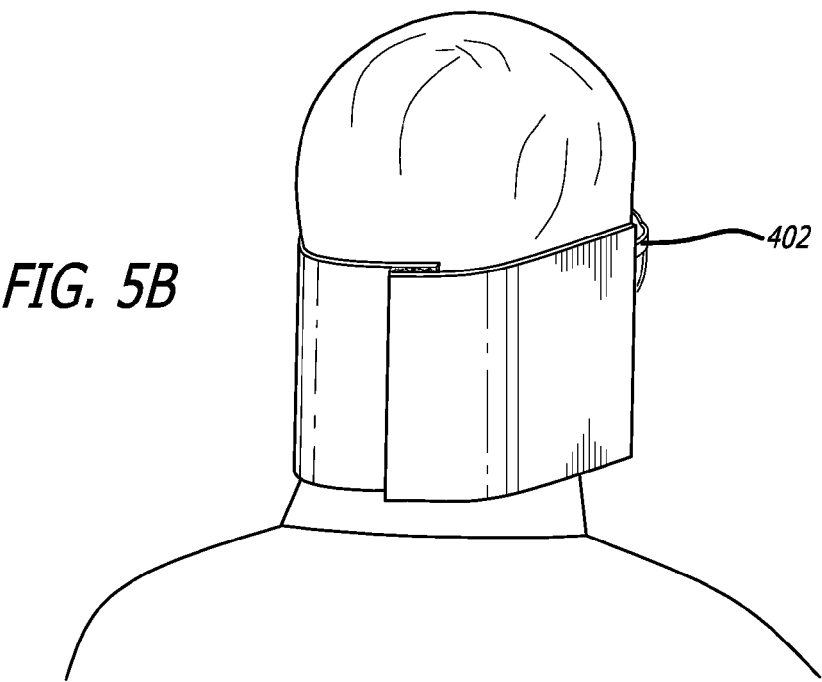

The use of these spectacle attachments 300 is similar to those described above except that, when worn, they can couple, e.g. behind the head of the user. The wearing of two spectacle attachments that are configured to couple with one another is illustrated in FIGS. 5A and 5B. Each spectacle attachment is attached to a respective temple 402. The spectacle attachments may then couple with one another behind the wearer's head, or at any other point along the relative length of the combined spectacle attachments.

When used together, these spectacle attachments can provide shade and protection to both sides of a user's face, and can further provide shade and protection to the user's neck. Alternatively, these spectacle attachments may be used independently of one another. Thus, a wearer may decide whether he wants to shade one side of the face or both sides of the face. Moreover, when a spectacle attachment that includes a magnetic strip is used independently of a corresponding such spectacle attachment, the magnetic strip can provide the spectacle attachment with rigidity that and/or structural support that can aide the isolated use of a single such spectacle attachment. For instance, the weight and rigidity of the magnetic strip can cause the spectacle attachment to rest against the back of the wearer's neck.

Figure 6:
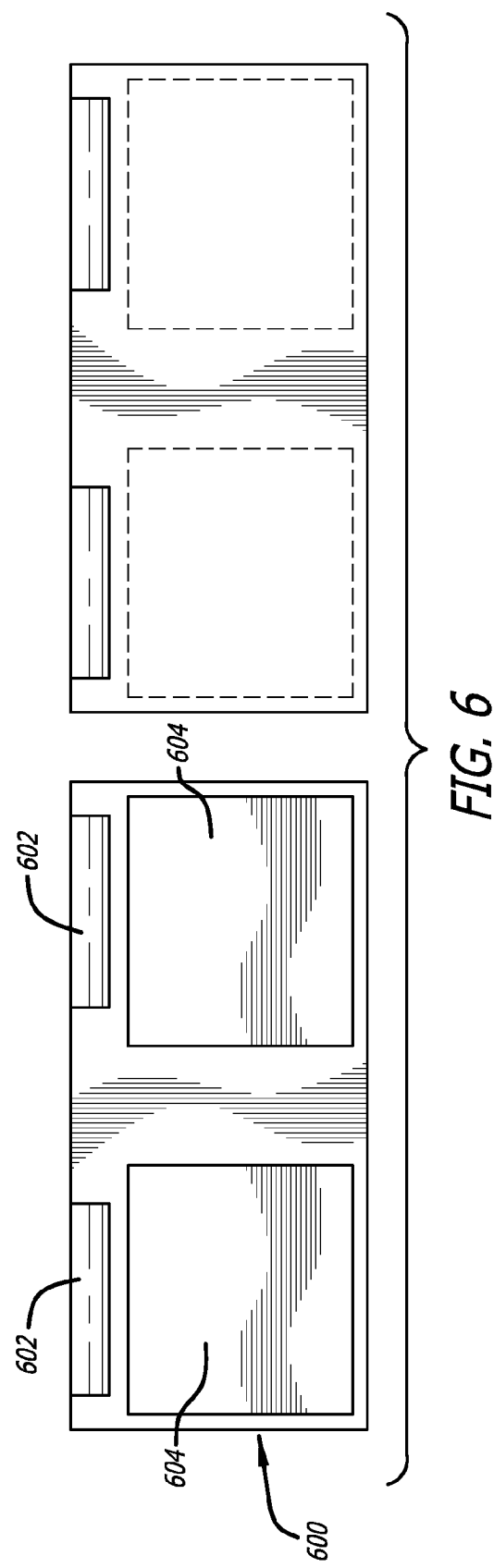
FIG. 6 illustrates a spectacle attachment that is configured to couple with another spectacle attachment such that the coupled spectacle attachments can protect either the front of a wearer's face or the back of the wearer's neck in accordance with an embodiment of the invention.

In a number of embodiments, spectacle attachments can be configured to interconnect with other spectacle attachments, such that either the back of the wearer's neck or the wearer's face can be additionally protected. FIG. 6 illustrates a pair of spectacle attachments that are configured to interconnect either in front of a wearer's face or behind the wearer's head, such that either the back of the wearer's neck or the wearer's face can also be protected. The spectacle attachments in the illustrated embodiment are similar to those seen in FIG. 3, except that each spectacle attachment includes two sleeves 602 and two magnetic strips 604, so that the spectacle attachments can either couple behind the wearer's head or in front of the wearer's face. For example, the rear sleeves may be used to couple the spectacle attachments to the pair glasses so that the body of material can extend beyond the face, and then wrap around and interconnect in front of the face via the magnetic strips. Alternatively, the forward sleeves may be used to couple the spectacle attachments to the pair of glasses, so that the body of material can extend beyond the back of the head, and then wrap around and interconnect behind the head via the magnets. In this way, either the back of the wearer's neck can be protected or the wearer's face can be protected. Of course, spectacle attachments can be configured to interconnect with each other either in front of the wearer's face or behind the wearer's head (or at any other point along the relative length of the combined spectacle attachments) in any suitable fashion. For example, although in the illustrated embodiment, magnets are used to interconnect the spectacle attachments, in some embodiments Velcro is used to interconnect two spectacle attachments.

Figure 7:
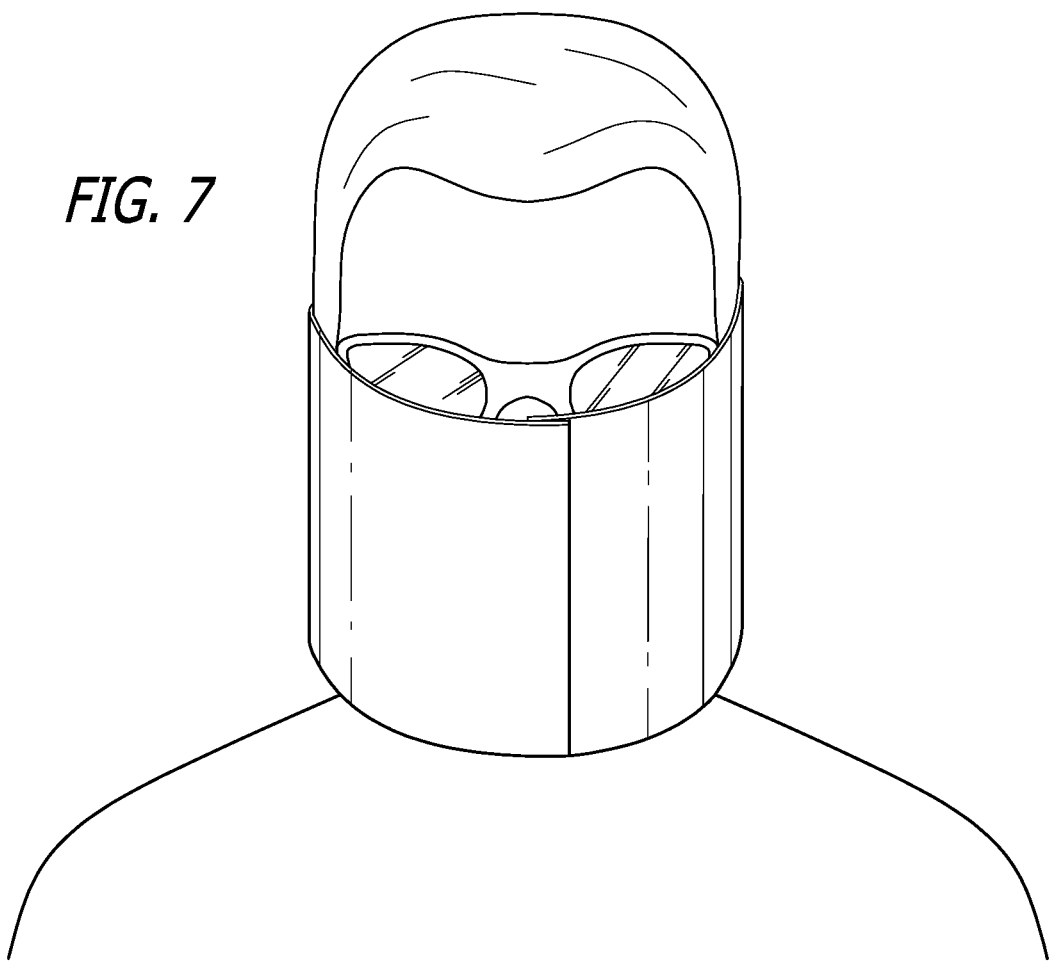
FIG. 7 illustrates the wearing of spectacle attachments that are configured to couple with one another and protect the front of a wearer's face in accordance with an embodiment of the invention.

The wearing of two spectacle attachments that can interconnect in front of the wearer's face is illustrated in FIG. 7. The demonstration is similar to that seen in FIGS. 5A and 5B, except that the attachments interconnect in front of the wearer's face. The weight of the spectacle attachments can cause them to sag, and thereby not obstruct the wearer's line of sight.

Although particular spectacle attachments that can couple with one another are described, any of a variety of spectacle attachments that couple with one another may be implemented in accordance with embodiments of the invention. For example, spectacle attachments that utilize a coupling mechanism other than magnets may be implemented in accordance with embodiments of the invention. Additionally, although a particular pair of spectacle attachments that can interconnect either in front of a wearer's face or behind a wearer's head has been elaborated on, this functionality can be achieved in any number of ways in accordance with embodiments of the invention. For example, a spectacle attachment that uses a single sleeve that is centrally disposed and can thereby allow the body of material to extend either in front of the face or behind the head, and that further that incorporates two magnets that can allow the spectacle attachment to interconnect with another one either in front of the face or behind the head can be implemented in accordance with embodiments of the invention. In a number of embodiments, a spectacle attachment that couples to both temples of a pair of glasses and thereby provides for protection for both sides of the face is provided, and these embodiments are discussed below.

Figure 8:
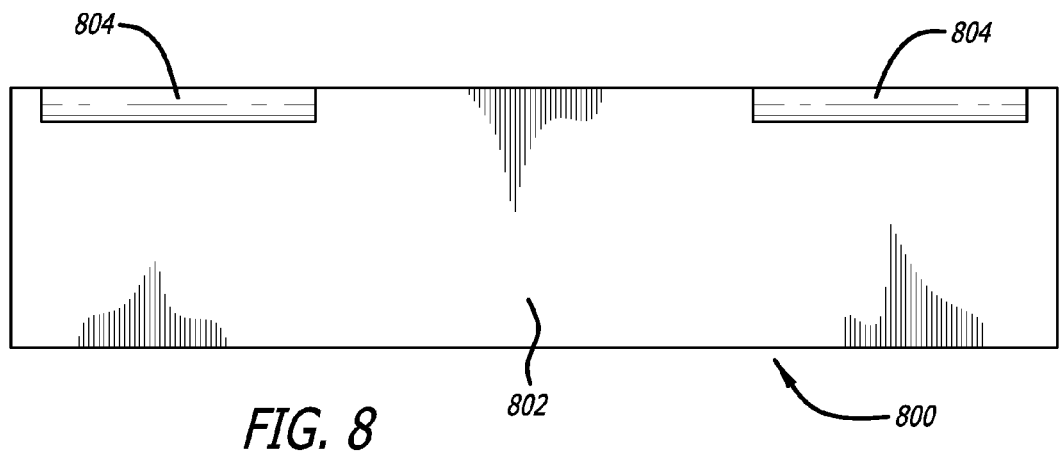
FIG. 8 illustrates a spectacle attachment that couples with both temples of a pair of glasses in accordance with an embodiment of the invention.

Spectacle Attachments that Couple with Both Temples of a Pair of Glasses to Provide Protection Spectacle attachments can be configured to couple with both temples of a pair of glasses and thereby provide protection to both sides of a face in accordance with embodiments of the invention. A spectacle attachment that includes a pliable material and two sleeves for coupling to both temples of a pair of glasses is illustrated in FIG. 8. The spectacle attachment 800 is similar to those described above with respect to FIGS. 1 and 3, except that the material 802 is sized to be able to couple with both temples of a pair of glasses, and thereby provide shade for both sides of a wearer's face simultaneously. As before, any suitable material that can provide shade for a wearer's face may be used in accordance with embodiments of the invention. In the illustrated embodiment, the spectacle attachment includes sleeves 804 to couple with the temples of a pair of glasses. However, as before, the spectacle attachment may couple to both temples of a pair of glasses in any suitable manner including, but not limited to, using: sleeves, loops, elastic holes, latches, clips, etc.

Figure 9:
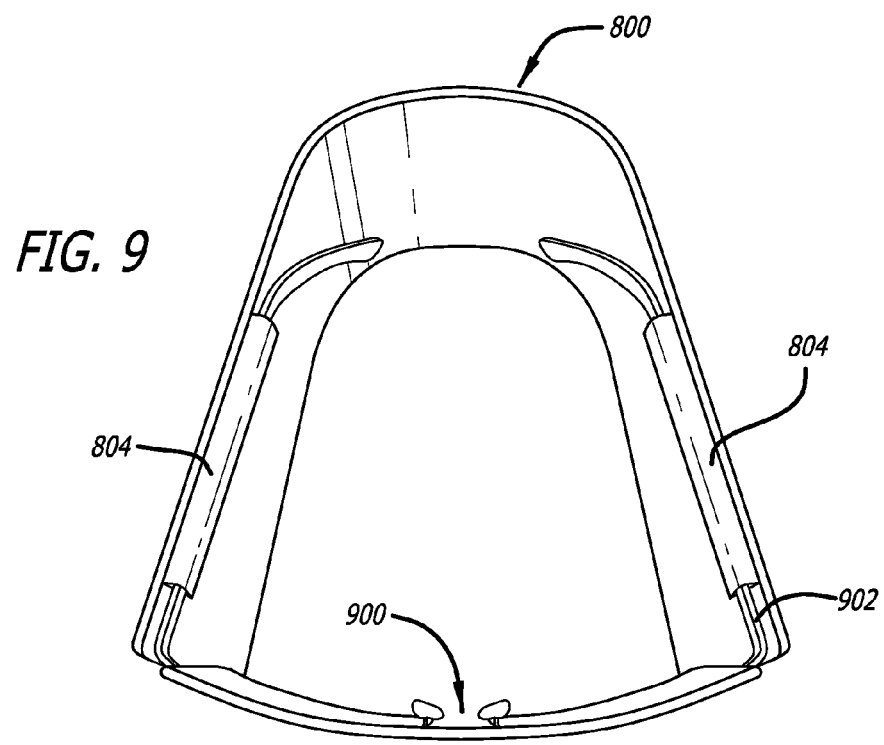
FIG. 9 illustrates the how a spectacle attachment can couple with both temples of a pair of glasses in accordance with an embodiment of the invention.

The coupling of a spectacle attachment that couples to both temples of a pair of glasses is illustrated in FIG. 9. The manner of coupling is similar to that recited before with respect to FIG. 4, except that the spectacle attachment 800 couples to both temples 902 of a pair of glasses 900. In the illustrated embodiment, sleeves 804 are used to couple the spectacle attachment to the pair of glasses 900.

Additionally, similar to before, spectacle attachments that couple with both temples of a pair of glasses can be configured to additionally protect either the back of a wearer's neck or the wearer's face. For instance, if the spectacle attachment is worn as illustrated in FIG. 9, the back of the wearer's neck may be protected. Alternatively, the wearing of the spectacle attachment seen in FIG. 9 can be reversed such that the wearer's face would be protected if worn in that manner.

While the above description contains many specific embodiments of the invention, these should not be construed as limitations on the scope of the invention, but rather each as an example of one embodiment thereof. Accordingly, the scope of the invention should be determined not by the embodiments illustrated and/or described, but by any recited claims and their equivalents.

What is claimed is:

1. A spectacle attachment that provides protection from radiation comprising:
    a body of material that is a barrier to one of: ultraviolet radiation, infrared radiation, visible light, and combinations thereof;
wherein the material that constitutes the body of material is a propylene fabric;
    wherein the body of material comprises a sleeve configured to allow the body of material to couple with a temple of a pair of glasses;
    wherein the body of material is sized to protect the side of a wearer's face from at least approximately the wearer's temple to approximately below the wearer's cheek when the body of material is coupled to a temple of a pair of glasses and the pair of glasses is worn; and
    wherein the body of material is further configured to interconnect with another spectacle attachment.

2. The spectacle attachment of claim 1, wherein the body of material is configured to interconnect with another spectacle attachment using a magnet that is affixed to the body of material.

3. The spectacle attachment of claim 2, wherein the magnet is sewn within the body of material.

4. The spectacle attachment of claim 2, wherein the magnet is sewn onto the exterior of the body of material.

5. The spectacle attachment of claim 1, wherein the body of material is configured to interconnect with another spectacle attachment using velcro.

6. A spectacle attachment that provides protection from radiation comprising:
    a body of material that is a barrier to one of: ultraviolet radiation, infrared radiation, visible light, and combinations thereof;
wherein the material that constitutes the body of material is a propylene fabric;
    wherein the body of material comprises a first sleeve configured to allow the body of material to couple with a temple of a pair of glasses;
    wherein the body of material is sized to protect the side of a wearer's face from at least approximately the wearer's temple to approximately below the wearer's cheek when the body of material is coupled to a temple of a pair of glasses and the pair of glasses is worn;
    wherein the body of material further comprises a second sleeve;
    wherein the first sleeve is proximate a first edge of body of material; and
    wherein the second sleeve is proximate a second edge that is opposite the first edge of the body of material;
    such that the body of material can couple to either temple of a pair of glasses and thereby provide protection; and
    wherein the body of material is further configured to interconnect with another spectacle attachment.

7. The spectacle attachment of claim 6, wherein the body of material is configured to interconnect with another spectacle attachment using at least two magnets that are affixed to the body of material;
    wherein a first magnet is disposed proximate the first edge of the body of material;

wherein the second magnet is disposed proximate the second edge of the body of material;

such that two spectacle attachments that are each coupled to a temple of a pair of glasses that is worn can interconnect either in front of the wearer's face or behind the wearer's head.

8. The spectacle attachment of claim 7, wherein the magnets are sewn within the body of material.

9. The spectacle attachments of claim 7, wherein the magnets are sewn onto the body of material.

* * * * *